(12) United States Patent
Hammer et al.

(10) Patent No.: US 8,709,051 B2
(45) Date of Patent: Apr. 29, 2014

(54) MULTI-AXIAL CONNECTION SYSTEM

(75) Inventors: Michael A. Hammer, Pine Brook, NJ (US); Alan Lombardo, Kinnelon, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 544 days.

(21) Appl. No.: 12/752,635

(22) Filed: Apr. 1, 2010

(65) Prior Publication Data

US 2010/0256681 A1    Oct. 7, 2010

Related U.S. Application Data (63) Continuation of application No. 10/928,955, filed on Aug. 27, 2004, now abandoned.

(51) Int. Cl.
*A61B 17/70* (2006.01)
*A61B 17/86* (2006.01)

(52) U.S. Cl.
USPC .......................... 606/272; 606/266; 606/308

(58) Field of Classification Search
USPC ......... 606/264–277, 246, 300, 301, 304–308, 606/328
See application file for complete search history.

(56) References Cited

U.S. PATENT DOCUMENTS

| | | |
|---|---|---|
| 4,946,458 A | 8/1990 | Harms et al. |
| 5,207,678 A | 5/1993 | Harms et al. |
| 5,443,467 A | 8/1995 | Biedermann et al. |
| 5,466,237 A | 11/1995 | Byrd, III et al. |
| 5,474,555 A | 12/1995 | Puno et al. |
| 5,496,321 A | 3/1996 | Puno et al. |
| 5,643,261 A | 7/1997 | Schafer et al. |
| 5,647,873 A | 7/1997 | Errico et al. |
| 5,669,911 A | 9/1997 | Errico et al. |
| 5,690,630 A | 11/1997 | Errico et al. |
| 5,733,286 A | 3/1998 | Errico et al. |
| 5,782,831 A | 7/1998 | Sherman et al. |

(Continued)

FOREIGN PATENT DOCUMENTS

| | | |
|---|---|---|
| JP | 2002315756 A | 10/2002 |
| WO | W09812976 | 4/1998 |

(Continued)

OTHER PUBLICATIONS

Definitions of "Integrate" from Dictionary.com, Accessed Jun. 21, 2010, 5 pages.

(Continued)

*Primary Examiner* — Michael T Schaper
(74) *Attorney, Agent, or Firm* — Baker & McKenzie LLP (57) ABSTRACT

In one embodiment of the present invention a system for connecting a fastener element (e.g., a pedicle screw) relative to a rod for the purposes of vertebral fixation is provided. The system may permit multi-axial movement between the fastener element and the rod. Further, the system may permit the angular relationship between the fastener element and the rod to be held in a desired orientation. For the purposes of describing and claiming the present invention, the term "rod" is intended to refer to any elongated structure. Such an elongated structure may be solid or hollow and may have any desired cross-section (e.g., circular, oval, square, rectangular). Further, for the purposes of describing and claiming the present invention, the term "interference fit" is intended to refer to physical contact between two or more components.

34 Claims, 5 Drawing Sheets

(56) References Cited

U.S. PATENT DOCUMENTS

| | | |
|---|---|---|
| 5,797,911 A | 8/1998 | Sherman et al. |
| 5,817,094 A | 10/1998 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,964,760 A | 10/1999 | Richelsoph |
| 5,997,539 A | 12/1999 | Errico et al. |
| 6,050,997 A | 4/2000 | Mullane |
| 6,063,090 A | 5/2000 | Schlapfer |
| 6,113,601 A | 9/2000 | Tatar |
| 6,187,005 B1 | 2/2001 | Brace et al. |
| 6,248,105 B1 | 6/2001 | Schlapfer et al. |
| 6,280,442 B1 | 8/2001 | Barker et al. |
| RE37,665 E * | 4/2002 | Ralph et al. ............... 606/278 |
| 6,383,190 B1 | 5/2002 | Preissman |
| 6,436,100 B1 | 8/2002 | Berger |
| 6,558,387 B2 | 5/2003 | Errico et al. |
| 6,565,565 B1 | 5/2003 | Yuan et al. |
| 6,582,436 B2 | 6/2003 | Schlapfer et al. |
| 6,613,050 B1 | 9/2003 | Wagner et al. |
| 6,641,586 B2 | 11/2003 | Varieur |
| 6,660,004 B2 | 12/2003 | Barker et al. |
| 6,740,086 B2 | 5/2004 | Richelsoph |
| 6,755,830 B2 | 6/2004 | Minfelde et al. |
| 6,905,500 B2 | 6/2005 | Jeon et al. |
| 6,951,561 B2 | 10/2005 | Warren et al. |
| RE39,089 E | 5/2006 | Ralph et al. |
| 7,081,116 B1 | 7/2006 | Carly |
| 7,087,057 B2 | 8/2006 | Konieczynski et al. |
| 7,141,051 B2 * | 11/2006 | Janowski et al. ............ 606/272 |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,338,490 B2 | 3/2008 | Ogilvie et al. |
| 7,476,239 B2 | 1/2009 | Jackson |
| 8,062,339 B2 | 11/2011 | Hammer et al. |
| 2001/0021852 A1 | 9/2001 | Chappius |
| 2002/0103487 A1 | 8/2002 | Errico et al. |
| 2003/0004512 A1 | 1/2003 | Farris |
| 2003/0045879 A1 | 3/2003 | Minfelde et al. |
| 2003/0100896 A1 | 5/2003 | Biedermann et al. |
| 2003/0163133 A1 | 8/2003 | Altarac et al. |
| 2003/0216735 A1 | 11/2003 | Altarac et al. |
| 2004/0024464 A1 | 2/2004 | Errico et al. |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 * | 7/2004 | Landry et al. ............... 606/61 |
| 2004/0153068 A1 | 8/2004 | Janowski et al. |
| 2004/0193160 A1 | 9/2004 | Richelsoph |
| 2004/0243126 A1 | 12/2004 | Carbone et al. |
| 2004/0267264 A1 | 12/2004 | Konieczynski et al. |
| 2005/0033289 A1 | 2/2005 | Warren et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0203515 A1 | 9/2005 | Doherty et al. |
| 2005/0228379 A1 * | 10/2005 | Jackson ...................... 606/61 |
| 2005/0228392 A1 | 10/2005 | Keyer et al. |
| 2005/0261687 A1 | 11/2005 | Garamszegi et al. |
| 2006/0015105 A1 | 1/2006 | Warren et al. |
| 2006/0149241 A1 | 7/2006 | Richelsoph |
| 2006/0161153 A1 | 7/2006 | Hawkes et al. |
| 2006/0241599 A1 | 10/2006 | Konieczynski et al. |
| 2006/0241600 A1 | 10/2006 | Ensign et al. |
| 2007/0055235 A1 | 3/2007 | Janowski et al. |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi et al. |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0097436 A1 | 4/2008 | Culbert et al. |
| 2008/0183216 A1 | 7/2008 | Jackson |
| 2010/0094349 A1 | 4/2010 | Hammer et al. |

FOREIGN PATENT DOCUMENTS

| | | |
|---|---|---|
| WO | 0122893 | 4/2001 |
| WO | 2004041100 | 5/2004 |
| WO | 2004071339 | 8/2004 |
| WO | 2005020829 A1 | 3/2005 |

OTHER PUBLICATIONS

International Search Report, PCT/US2006/010738, dated Aug. 17, 2007, 3 pages.

Written Opinion, PCT/US2006/010738, dated Aug. 17, 2007, 4 pages.

International Preliminary Report on Patentability, PCT/US2006/010738, dated Sep. 25, 2007, 5 pages.

European Extended Search Report, EP Appl. No. 05789259.8-2310 / PCT/US2005/029836, dated May 20, 2009, 7 pages.

* cited by examiner

MULTI-AXIAL CONNECTION SYSTEM

CROSS-REFERENCE TO RELATED APPLICATIONS

This application is a continuation of U.S. patent application Ser. No. 10/928,955 filed on Aug. 27, 2004, now abandoned which is expressly incorporated herein in its entirety by reference thereto.

FIELD OF THE INVENTION

In one embodiment of the present invention a system for connecting a fastener element (e.g., a pedicle screw) relative to a rod for the purposes of vertebral fixation is provided. The system may permit multi-axial movement between the fastener element and the rod. Further, the system may permit the angular relationship between the fastener element and the rod to be held in a desired orientation.

For the purposes of describing and claiming the present invention, the term "rod" is intended to refer to any elongated structure. Such an elongated structure may be solid or hollow and may have any desired cross-section (e.g., circular, oval, square, rectangular).

Further, for the purposes of describing and claiming the present invention, the term "interference fit" is intended to refer to physical contact between two or more components.

BACKGROUND OF THE INVENTION

Various systems for connecting fastener elements (e.g., pedicle screws) to elongated supports (e.g., rods) for the purposes of vertebral fixation have been proposed. Examples include the systems described in the following U.S. patents.

U.S. Pat. No. 5,466,237 relates to a variable locking stabilizer anchor seat and screw. More particularly, this patent relates to a bone interface anchor provided for use with a stabilizer rod for the internal fixation of a spine. The anchor has a seat which accommodates the stabilizer rod and which receives a bone screw for the fixation of the seat to the bone. A compression member cooperates with the seat external to the stabilizer rod and can be tightened to cause a compressive force on the stabilizer rod. The stabilizer rod bears on a rounded surface of the bone screw so as to cause a mating interface between the seat and the bone screw. Subsequently, the position of the seat relative to the bone screw can be locked.

U.S. Pat. No. 5,474,555 relates to a spinal implant system. More particularly, this patent relates to an apparatus for the internal fixation of the spine. The apparatus comprises an assembly having at least two anchors and an elongated stabilizer. The anchors each have means to hold the anchor to the bone, and include receiving means which receive the stabilizer as well as securing means which cooperate with the receiving means by means of the interaction of mating threads to cause the application of compression on the stabilizer into the receiving means.

U.S. Pat. No. 5,669,911 relates to a polyaxial pedicle screw. More particularly, this patent relates to a polyaxial orthopedic device for use with rod implant apparatus. The device includes a screw having a curvate head, a locking collar disposed therearound, and a receiving member having a linearly tapered socket in which the screw and the collar are nested. The locking collar is slotted and tapered, and has a semi-spherical interior volume into which the screw head is initially polyaxially held. The receiving member has a transverse channel formed in it for receiving a rod, and an axial bore having a linearly tapered chamber in the bottom portion thereof. The collar is inserted down the bore from the top to seat in the chamber, and the screw is subsequently inserted up through the bottom of the bore and into the collar. The linear taper of the chamber provides a radially inward force on the locking collar when the collar is forced downward therein. This radially inward force causes the locking collar to crush lock against the head of the screw, therein locking the two at the given angulation. It is the placement of the rod in the transverse channel, against the top of the collar, and the subsequent locking down of the rod in the channel which provides the downward force against the locking collar, which in turn locks the screw in its given angulation.

U.S. Pat. No. 5,879,350 relates to a multi-axial bone screw assembly. More particularly, this patent relates to a multi-axial bone screw assembly including a bone screw having a partially spherical head. The bone screw head is truncated at an upper surface in which a tool receiving recess is defined. The assembly includes a receiver member including a central bore that defines a tapered recess to receive a contracting collet carrying the head of the bone screw. The bore of the receiver member also defines a channel communicating with the recess and configured to receive a spinal rod therein. A portion of the channel is threaded to receive a set screw above the rod. The assembly also includes a contracting collet disposed between the rod and the head of the bone screw. The collet defines a partially spherical recess to receive the head of the bone screw, and includes deflectable fingers that substantially surround the screw head. As the set screw is tightened into the receiver member, the set screw compresses the rod against the collet, which presses the collet into the tapered recess of the receiver member, thereby deflecting the fingers of the collet against the bone screw head.

U.S. Pat. No. 6,063,090 relates to a device for connecting a longitudinal support to a pedicle screw. More particularly, this patent relates to a device used to connect a longitudinal support to a pedicle screw by an accommodating head having a channel to accommodate the longitudinal support, wherein it is possible to freely choose from or mix laterally open, top open or closed accommodating heads. A top open accommodating head facilitates, for example, insertion of the longitudinal support, whereas a lateral opening enables lateral corrections. The pedicle screw and the accommodating head are connected via a conical collet chuck in the accommodating head and by a spherical head on the pedicle screw. The present invention allows engagement of the pedicle screw in the accommodating head after the pedicle screw has been inserted into bone.

U.S. Pat. No. 6,582,436 relates to a device for connecting a longitudinal support to a bone anchor. More particularly, this patent relates to a device for connecting a longitudinal support to a bone anchor having a rounded head. The device includes a body defining a chamber for receiving the rounded head of the bone anchor and a first channel for receiving the longitudinal support. Further, a first sleeve is slidable over the body for compressing the chamber, a second sleeve is slidable over the body for biasing the longitudinal support against the first sleeve, and a fastener is operatively associated with the body for biasing the second sleeve toward the first sleeve. The forces exerted on the second sleeve by the fastener are transferred to the first sleeve in a plane perpendicular to the central axis. Preferably, the longitudinal support contacts the first sleeve at first and second contact points or zones and one of the sleeves includes at least one extended portion for contacting the other sleeve at least one additional contact point or zone.

U.S. Pat. No. 6,660,004 relates to a multi-axial bone screw assembly. More particularly, this patent relates to a bottom-loading multi-axial bone anchor apparatus. The apparatus includes a receiver member, a crown member, a bone anchor and a retaining member. The receiver member defines an upper opening and a lower opening, which may form part of the same opening, a channel, and a groove. The crown member and bone anchor are loaded into the lower opening of the receiver member, and the retaining member fits around the bone anchor and into the groove in the receiver member. The bone anchor is capable of multi-axial positioning with respect to the receiver member. An elongated member is placed in the channel of the receiver member, contacting the crown member, and a compression member is applied via the upper opening. The compression member presses down on the elongated member, which presses down on the crown member and locks the bone anchor between the crown member and the retaining member.

U.S. Pat. No. 6,740,086 relates to a screw and rod fixation assembly and device. More particularly, this patent relates to a screw and rod fixation assembly for fixing a screw and, optionally, a rod. The screw and rod fixation assembly includes a screw, fixing mechanism, a substantially annular ring, rod seating mechanism, and locking mechanism. The present invention also provides for a fixing mechanism for fixing a screw, wherein the fixing mechanism further includes an inner surface wall having a gripping portion and a non-gripping portion. Further, the present invention provides for a substantially annular ring for guiding and providing mechanical and frictional force to a screw head. Additionally, the present invention provides for a rod seating mechanism operatively engaged to the screw head and including at least one flexible portion capable of being compressed against a portion of a rod therein. Finally, the present invention provides for a linking mechanism for engaging the rod and the rod seating mechanism. The locking mechanism includes a deflecting mechanism for deflecting the at least one flexible portion of the rod seating mechanism against and around the rod as the locking mechanism further engages the at least one flexible portion of the rod seating mechanism.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
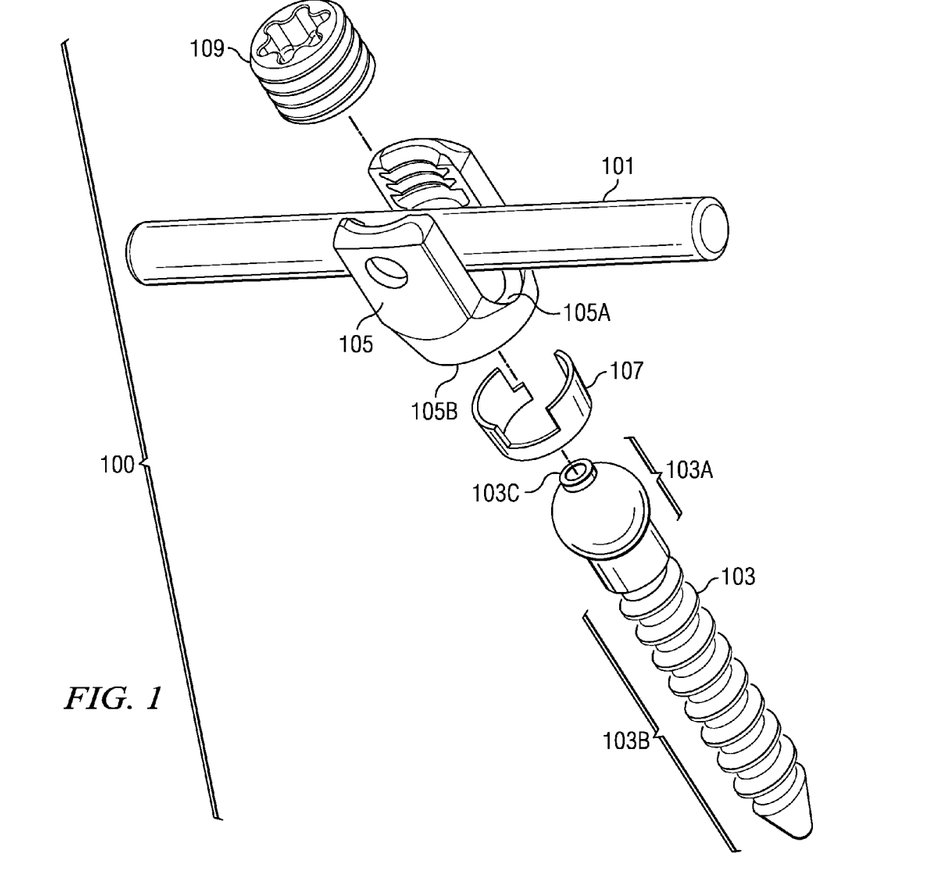
FIG. 1 shows an exploded perspective view of a fastener assembly according to an embodiment of the present invention.
Figure 2:
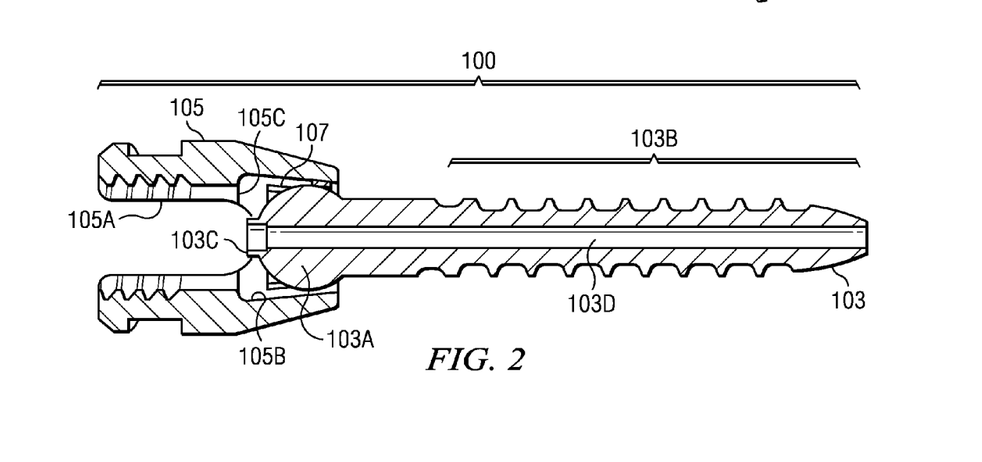
FIG. 2 shows a cross-sectional view of a partially assembled fastener assembly according to the embodiment of FIG. 1 (for clarity, this Fig. does not include the rod or compression member of FIG. 1)

Referring now to FIGS. 1 and 2, a first embodiment of the present invention is shown. As seen in these Figs., Fastener Assembly 100 may be used in connection with mounting Rod 101 relative to a spine of a patient (of course, one or more such Fastener Assemblies may be used with one or more Rods). More particularly, Fastener Assembly 100 may include Fastener 103 having Head 103A at a first end and Bone Connection Element 103B at a second end (Bone Connection Element 103B may be adapted for attachment on, in and/or to the spine). Further, Head 103A may include at least one Deformation Element 103C thereon.

In one example (which example is intended to be illustrative and not restrictive), at least a portion of Head 103A may be spherical. In another example (which example is intended to be illustrative and not restrictive), Fastener 103 may be a bone screw and Bone Connection Element 103B may comprise threads. In another example (which example is intended to be illustrative and not restrictive), Fastener 103 may be a cannulated bone screw (see Cannulation 103D of FIG. 2). In another example (which example is intended to be illustrative and not restrictive), Deformation Element 103C may substantially surround Cannulation 103D (e.g., where Cannulation 103D exits Head 103A). In another example (which example is intended to be illustrative and not restrictive), Deformation Element 103C may be a substantially circular ring protruding from Head 103A. In another example (which example is intended to be illustrative and not restrictive), Deformation Element 103C (and/or any other portion of Fastener 103 (e.g., Head 103A or the entire Fastener 103)) may include a material which is: (a) softer than a material from which Rod 101 is formed; (b) harder than a material from which Rod 101 is formed; or (c) of essentially the same hardness as a material from which Rod 101 is formed (e.g., the same material from which Rod 101 is formed).

Still referring to FIGS. 1 and 2, it is seen that Fastener Assembly 100 may include Body 105. Body 105 may have a first end and a second end, wherein Rod Receiving Channel 105A for receiving Rod 101 is disposed adjacent the first end of Body 105 and Fastener Head Receiving Chamber 105B is disposed adjacent the second end of Body 105 (as seen in these Figs., Fastener Head Receiving Chamber 105B may be tapered towards the second end of Body 105 and Rod Receiving Channel 105A and Fastener Head Receiving Chamber 105B may be operatively connected (e.g., a hole in Body 105 may connect Rod Receiving Channel 105A and Fastener Head Receiving Chamber 105B)).

Further, Fastener Assembly 100 may include Retention Ring 107. This Retention Ring 107 may be sized to fit at least partially around Head 103A when Head 103A is disposed within Fastener Head Receiving Chamber 105B. In one example (which example is intended to be illustrative and not restrictive), Retention Ring 107 may be, as shown in the Figs., of a "split-ring" design.

Further still, Compression Element 109 may cooperate with Body 105 to push Rod 101, when Rod 101 is disposed within Rod Receiving Channel 105A, into contact with at least part of Deformation Element 103C. Such contact between Rod 101 and Deformation Element 103C will deform Deformation Element 103C while pressing Head 103A towards the tapered end narrower end) of Fastener Head Receiving Chamber 105B. This action will serve to fix the angular relationship of Fastener 103 relative to Rod 101.

More particularly, the angular relationship of Fastener 103 relative to Rod 101 may be fixed at least in part due to: (a) an interference fit (caused by radial compression) between at least a portion of an outside surface of Head 103A and at least a portion of an inside surface of Retention Ring 107; (b) an interference fit (caused by radial compression) between at least a portion of an outside surface of Retention Ring 107 and at least a portion of an inside surface of Fastener Head Receiving Chamber 105B; and/or (c) an interference fit between at least a portion of an outside surface of Rod 101 and Deformation Element 103C.

In one example (which example is intended to be illustrative and not restrictive), Compression Element 109 may have threads which cooperate with complementary threads of Body 105. In another example (which example is intended to be illustrative and not restrictive), Compression Element 109 may have external threads which cooperate with complementary internal threads of Body 105 (e.g., Compression Element 109 may be a set screw). In another example (which example is intended to be illustrative and not restrictive), Compression Element 109 may have internal threads which cooperate with complementary external threads of Body 105 (e.g., Compression Element 109 may be a nut). In another example (which example is intended to be illustrative and not restrictive), Compression Element 109 may have one or more indentations, protrusions and/or drive faces for receiving torque from a drive tool (see, e.g., the female hex feature of FIG. 1).

Reference will now be made to the elements shown in FIGS. 1 and 2 in connection with the description of an example installation procedure. Such an example installation procedure is applicable to this embodiment of the fastener assembly of the present invention and, of course, is intended to be illustrative and not restrictive.

More particularly, a guide wire may first be attached to a pedicle of the spine. The free end of the guide wire may then be passed through Fastener 103 (via Cannulation 103D). Fastener 103 (e.g., a pedicle screw) may then be inserted (e.g., screwed into) the pedicle of the spine. Of note, such a pedicle screw may be self-tapping into a hole bored into the pedicle or the hole bored into the pedicle may be pre-tapped. Of further note, such a pedicle screw may be driven into bone with any desired tool (e.g., a hand or power driver applying torque through Rod Receiving Channel 105A and Fastener Head Receiving Chamber 105B).

In one example (which example is intended to be illustrative and not restrictive), such a pedicle screw may be driven into bone with a torque applying tool that engages one or more indentations, protrusions and/or drive faces on Head 103A (see, e.g., the four scallops of Head 103A in FIG. 1).

In one example (which example is intended to be illustrative and not restrictive), Fastener 103 may be driven into bone by itself. Next, a body/retention ring assembly (e.g., including Body 105 having Retention Ring 107 already disposed within Fastener Head Receiving Chamber 105B) may be placed (or "snapped") onto Fastener 103.

In this regard, as Body 105 is subsequently pushed onto Head 103A, Retention Ring 107 is pushed against the back wall of Fastener Head Receiving Chamber 105B (see 105C of FIG. 2) and Retention Ring 107 is free to expand outward enabling Head 103A to pass through. Once Head 103A pushes through the bottom of Retention Ring 107, Head 103A remains captured (since Retention Ring 107 would have no room to expand as it was pulled forward by Head 103A towards the tapered (i.e., narrowed) end of Fastener Head Receiving Chamber 105B.

Next, Rod 101 may be placed in Rod Receiving Channel 105A (with Rod 101 coming into contact with Deformation Element 1030.

Finally, as Compression Element 109 (e.g., a set screw) is threaded into Body 105, Compression Element 109 clamps the components in a set position (that is, Compression Element 109 pushes Rod 101 against Deformation Element 103C (and, depending upon the size and shape of Rod 101, Deformation Element 103C and Head 103A, against a portion of Head 103A)). Of note, during this clamping process Deformation Element 103C is deformed (e.g., to form a surface complementary to the portion of Rod 101 causing the deformation) and the result is improved locking (e.g., of the angular relationship between Rod 101 and Fastener 103). Of further note, it is believed that Deformation Element 103C is particularly useful in enabling secure locking of cannulated fasteners, such as cannulated pedicle screws (it is believed that a cannulation (without the use of a deformation element according to the present invention) may tend to compromise the ability to lock the multi-axial adjustability).

In another example (which example is intended to be illustrative and not restrictive), rather than driving Fastener 103 into bone by itself and then placing a body/retention ring assembly thereon, Fastener 103 may be captured within body/retention ring assembly as discussed above and then the entire body/retention ring/fastener assembly may be attached to the bone (e.g., by using a driving tool such as a hand or power driver to drive the pedicle screw through the hole provided in Body 105 between Rod Receiving Channel 105A and Fastener Head Receiving Chamber 105B).

Figure 3:
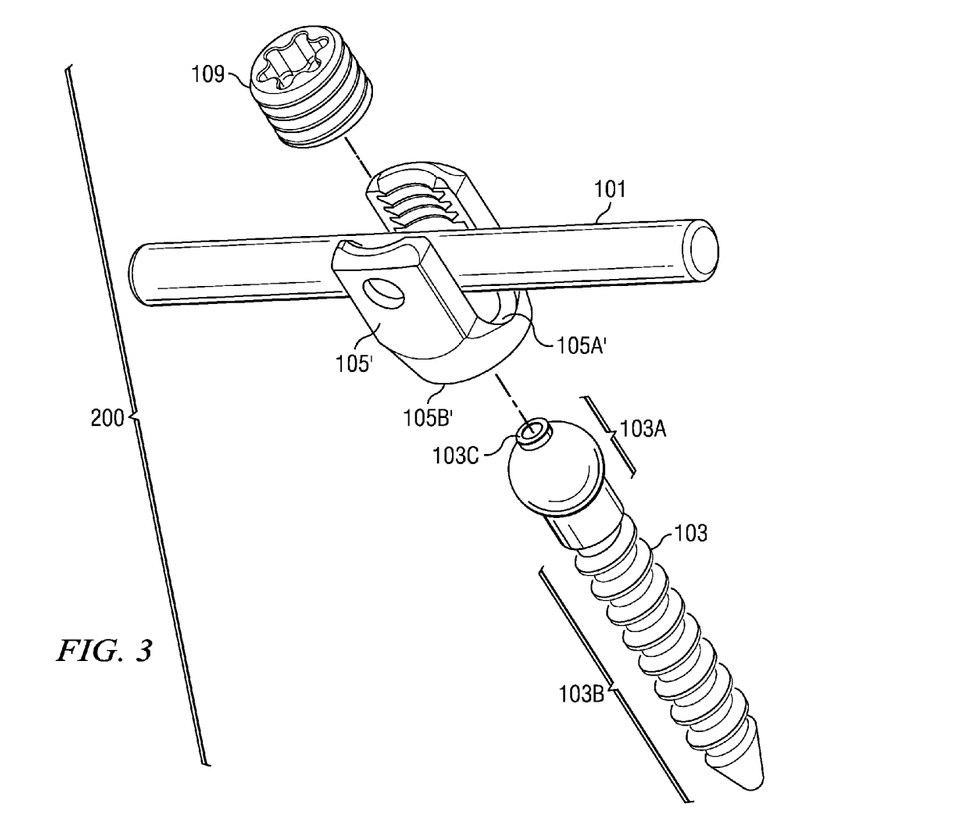
FIG. 3 shows an exploded perspective view of a fastener assembly according to another embodiment of the present invention.
Figure 4:
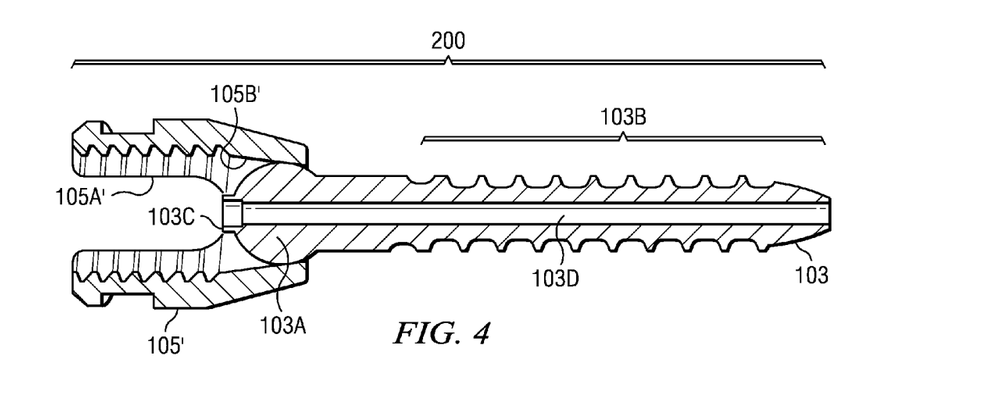
FIG. 4 shows a cross-sectional view of a partially assembled fastener assembly according to the embodiment of FIG. 3 (for clarity, this Fig. does not include the rod or compression member of FIG. 3).

Referring now to FIGS. 3 and 4, another embodiment of the present invention is shown. This embodiment is similar to the embodiment shown in FIGS. 1 and 2 and, in this regard, the same elements will be identified by the same reference numerals (such similar elements will not be described again in detail). Of note, the main difference between the embodiment of these FIGS. 3 and 4 and the embodiment of FIGS. 1 and 2 is that in this embodiment Fastener Assembly 200 does not utilize Retention Ring 107.

More particularly, Fastener Assembly 200 may again be used in connection with mounting Rod 101 relative to, a spine of a patient (of course, one or More Such Fastener Assemblies may be used with one or more Rods). Further, Fastener Assembly 200 may include Fastener 103 (having Head 103A, Bone Connection Element 103B and at least one Deformation Element 103C).

Still referring to FIGS. 3 and 4, it is seen that Fastener Assembly 200 may further include Body 105' (Body 105' may have a first end and a second end, wherein Rod Receiving Channel 105A' for receiving Rod 101 is disposed adjacent the first end of Body 105' and Fastener Head Receiving Chamber 105B' is disposed adjacent the second end of Body 105'). As seen in these Figs., Fastener Head Receiving Chamber 105B' may be tapered towards the second end of Body 105' and a hole may be disposed through Body 105' to connect Rod Receiving Channel 105A' and Fastener Head Receiving Chamber 105B'.

Of note, the tapered (i.e., narrow) end of Fastener Head Receiving Chamber 105B' may be made sufficiently small so as to prohibit Head 103A from passing therethrough (while Rod Receiving Channel 105A' and the hole in Body 105' connecting Rod Receiving Channel 105A' to Fastener Head Receiving Chamber 105B' may be made sufficiently large so as to allow Head 103A to pass therethrough).

In this regard, Fastener Assembly 200 may be installed by inserting Fastener 103 through Body 105' such that Head 103A comes to rest in Fastener Head Receiving Chamber 105B' (see FIG. 4). Fastener 103 may then be inserted (e.g., into the pedicle of the spine) as discussed above (e.g., a guide wire may be used to guide Fastener 103 and either a self-tapping bone screw may be driven into a hole in the bone or a pre-tapped hole in the bone may be provided).

Finally, Compression Element 109 may cooperate with Body 105' to push Rod 101, when Rod 101 is disposed within Rod Receiving Channel 105A', into contact with at least part of Deformation Element 103C to deform Deformation Element 103C while pressing Head 103A towards the tapered end (i.e., narrower end) of Fastener Head Receiving Chamber 105B. This action will fix the angular relationship of Fastener 103 relative to Rod 101 (the angular relationship of Fastener 103 relative to Rod 101 may be fixed at least in part due to: (a) an interference fit (caused by radial compression) between at least a portion of an outside surface of Head 103A and at least a portion of an inside surface of Fastener Head Receiving Chamber 105B'; and/or (b) an interference fit between at least a portion of an outside surface of Rod 101 and Deformation Element 103C.

Figure 5:
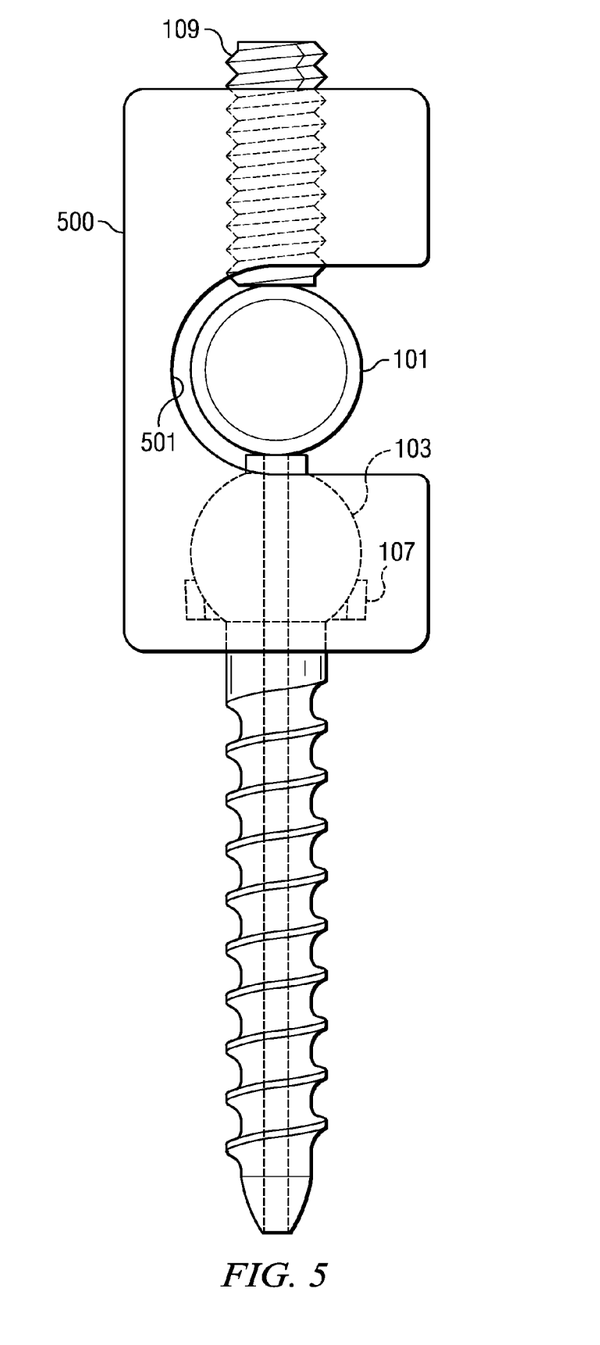
FIG. 5 shows a side view of a fastener assembly according to another embodiment of the present invention.
Figure 6:
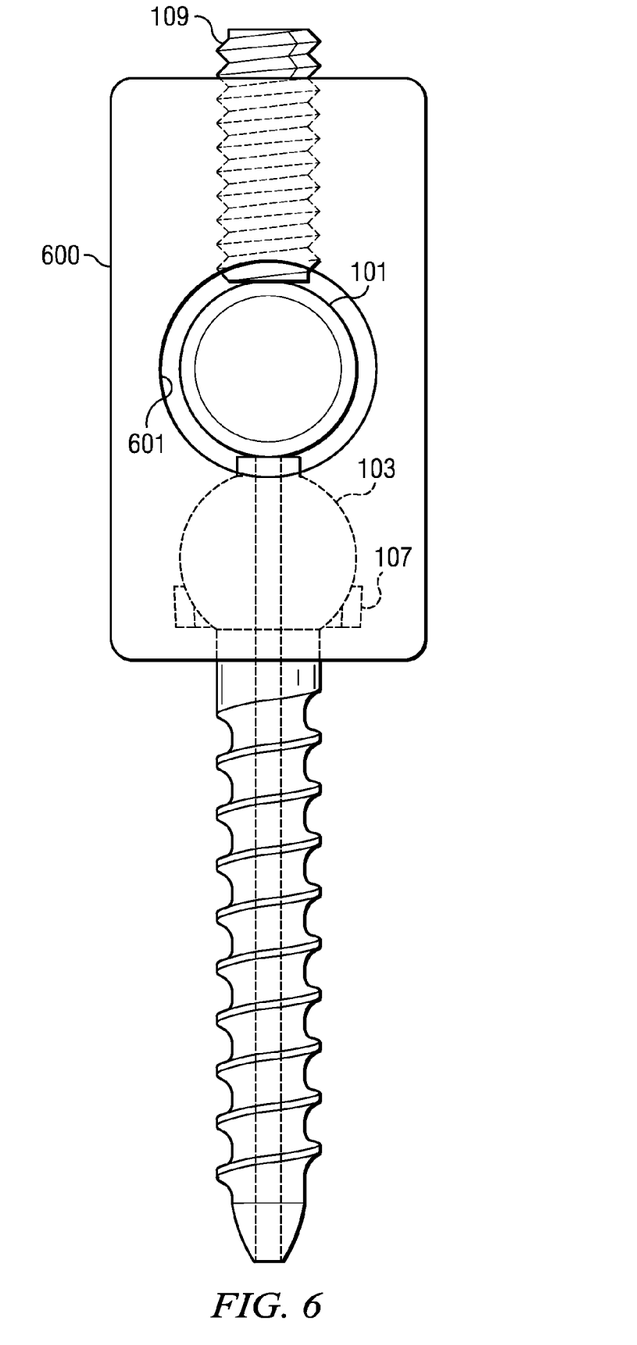
FIG. 6 shows a side view of a fastener assembly according to another embodiment of the present invention.

Referring now to FIGS. 5 and 6, two other embodiments of a fastener assembly body are shown. In this regard, it is noted that Body 105 of FIGS. 1 and 2 has an upward facing Rod Receiving Channel 105A for receiving Rod 101. Likewise, Body 105' of FIGS. 3 and 4 has an upward facing Rod Receiving Channel 105A' for receiving Rod 101. In contrast, it is seen in FIG. 5 that Body 500 includes a sideward facing Rod Receiving Channel 501 for receiving Rod 101 (Rod 101, Fastener 103, Compression Element 109 and Retention Ring 107 are shown in phantom and are essentially the same elements as described in detail above). Further, it is seen in FIG. 6 that Body 600 includes a "tunnel-type" Rod Receiving Channel 601 for receiving Rod 101 (Rod 101, Fastener 103, Compression Element 109 and Retention Ring 107 are shown in phantom and are essentially the same elements as described in detail above). Of note, the embodiments of these FIGS. 5 and 6 may operate as discussed above (e.g., the body may include a tapered chamber for facilitating an interference fit between the components disposed therein).

Figure 7:
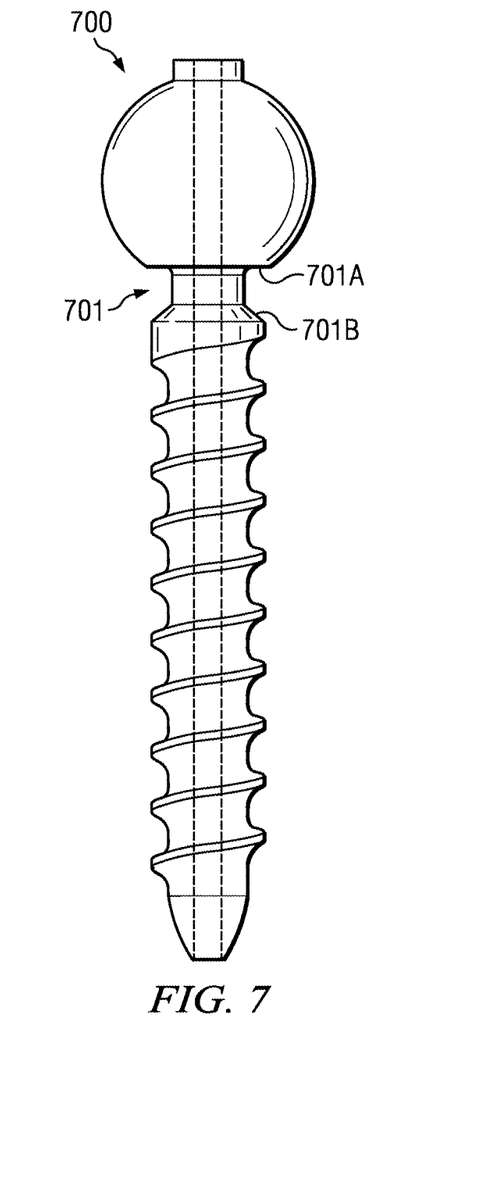
FIG. 7 shows a side view of a fastener according to an embodiment of the present invention.

Referring now to FIG. 7, another embodiment of a fastener for use with the present invention is shown. Of note, Fastener 700 is depicted here as a bone screw, although other types of bone attaching mechanisms may, of course, be utilized (e.g., a shaft having a hook on the end). In any case, it is seen that in this embodiment Undercut 701 is provided (Undercut 701 may be formed, for example, by a flattening of the bottom of the head of the bone screw (see 701A) and/or by a narrowing of a portion of the shaft of the bone screw (see 701B)). By using such Undercut 701, Fastener 700 may provide increased clearance in the area where Fastener 700 extends from the body of the fastener assembly (wherein such increased clearance may translate into an increase in a maximum angle that Fastener 700 may obtain in relation to the fastener body and/or the rod.

While a number of embodiments of the present invention have been described, it is understood that these embodiments are illustrative only, and not restrictive, and that many modifications may become apparent to those of ordinary skill in the art. For example, the present invention may be placed at any desired level of the spine. Further, the present invention may be used in conjunction with a posterior spinal rod implantation. Further still, the controllable angulation provided by the present invention may be in any desired number of planes. Further still, the rod may be fixed axially and rotationally. Further still, any element described herein may be provided in any desired size (e.g., any element described, herein may be provided in any desired custom size or any element described herein may be provided in any desired size selected from a "family" of sizes, such as small, medium, large. To give a more specific example (which example is intended to be illustrative and not restrictive), a bone screw may be provided in a desired thread pitch, thread outer diameter, shaft outer diameter, shaft outer diameter to thread outer diameter ratio and/or length and a body element may be provided in any desired inner diameter, outer diameter and/or length. Further still, the compression element may have a "break-off" feature for separating from the installed portion of the compression element when a desired amount of torque has been applied. Further still, one or more of the components of the fastener assembly may be made from any of the following materials: (a) any biocompatible material (which biocompatible material may be treated to permit bone ingrowth or prohibit bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, use of the guide wire for guiding the fastener via the cannulation may be useful during a minimally invasive procedure, for example. Further still, the bone screw may be adapted for placement in cancellous bone. Further still, rather than a thread, the fastener may employ a hook for attachment to bone. Further still, an outer surface of the head of the fastener, an outer surface of the rod, an outer surface of the retention ring, an inner surface of the retention ring and/or an inner surface of the body (e.g., at any interface area between the aforementioned components) may have one or more features for increasing friction at the interface. For example, any of the aforementioned components may have: a roughened or treated surface (e.g., via sandblasting or knurling), a threaded surface, a grooved surface, a ridged surface, a surface with protrusions, and/or a surface with indentations. Further still, the deformation element may deform in dependence upon: (a) the material utilized for the deformation element; (b) the material utilized for the rod; (c) a geometry of the rod in the area where the rod contacts the deformation element; (d) a geometry of the deformation element; (e) a direction of a load applied to the deformation element by the rod; and/or (f) a magnitude of a load applied to the deformation element by the rod. Further still, a minimum of two-fastener assemblies for each rod may be used (e.g., for stabilization purposes). Further still, any steps described herein may be carried out in any desired order.

What is claimed is:

1. A spinal fixation system, comprising:
    at least one rod;
    at least one screw having a head at a first end, wherein the head of the screw comprises at least one deformation element portion, wherein the deformation element portion comprises an initial undeformed surface shape, and wherein the head of the screw and the deformation element portion are integrally formed;

at least one body, wherein the body has a first end and a second end, wherein a rod receiving channel is disposed adjacent the first end of the body, wherein a screw head receiving chamber is disposed adjacent the second end of the body, wherein the screw head receiving chamber is tapered towards the second end of the body, and wherein the rod receiving channel and the screw head receiving chamber are operatively connected; and a compression element which cooperates with the body to push the rod, when the rod is disposed within the rod receiving channel, into contact with at least part of the deformation element portion of the head of the screw to deform the deformation element portion while pressing the head of the screw towards the tapered end of the screw head receiving chamber to fix an angular relationship of the screw relative to the rod, wherein the deformed deformation element portion comprises a deformed surface shape complementary to a shape of the rod.

2. The spinal fixation system of claim 1, wherein the angular relationship of the screw relative to the rod is fixed at least in part due to: (a) an interference fit between at least a portion of an outside surface of the head of the screw and at least a portion of an inside surface of the screw head receiving chamber; and (b) an interference fit between at least a portion of an outside surface of the rod and the deformation element portion of the head of the screw.

3. The spinal fixation system of claim 1, further comprising a retention ring sized to fit at least partially around the head of the screw when the head of the screw is disposed within the screw head receiving chamber.

4. The spinal fixation system of claim 3, wherein the angular relationship of the screw relative to the rod is fixed at least in part due to: (a) an interference fit between at least a portion of an outside surface of the head of the screw and at least a portion of an inside surface of the retention ring; (b) an interference fit between at least a portion of an outside surface of the retention ring and at least a portion of an inside surface of the screw head receiving chamber; and (c) an interference fit between at least a portion of an outside surface of the rod and the deformation element portion of the head of the screw.

5. The spinal fixation system of claim 1, wherein the screw is a bone screw.

6. The spinal fixation system of claim 5, wherein the bone screw is configured to be screwed into a pedicle portion of a spine.

7. The spinal fixation system of claim 5, wherein the bone screw is a cannulated bone screw.

8. The spinal fixation system of claim 7, wherein the deformation element portion of the head of the cannulated bone screw substantially surrounds the cannulation in the bone screw.

9. The spinal fixation system of claim 1, wherein the deformation element portion of the head of the screw comprises a material which is selected from the group consisting of: (a) a material which is softer than a material from which the rod is formed; and (b) a material which is of essentially the same hardness as a material from which the rod is formed.

10. The spinal fixation system of claim 1, wherein the rod receiving channel and the screw head receiving chamber are operatively connected to allow a tool to be inserted therethrough to apply torque to the screw.

11. The spinal fixation system of claim 10, wherein the head of the screw is at least partially spherical.

12. The spinal fixation system of claim 10, wherein the head of the screw includes at least one torque receiving feature for receiving torque from the tool.

13. The spinal fixation system of claim 12, wherein the torque receiving feature is selected from the group consisting of: (a) at least one indentation; (b) at least one protrusion; and (c) at least one drive face.

14. The spinal fixation system of claim 1, wherein the rod has a substantially circular cross section.

15. The spinal fixation system of claim 1, wherein the compression element has threads which cooperate with complementary threads of the body.

16. The spinal fixation system of claim 15, wherein the compression element has external threads which cooperate with complementary internal threads of the body.

17. A fastener assembly, comprising:

a rod;

at least one fastener having a head at a first end and a bone connection element at a second end, wherein the head of the fastener comprises at least one deformation element portion and the bone connection element of the fastener is adapted for connection to a spine of a patient, wherein the deformation element portion comprises an initial undeformed surface shape, and wherein the head of the fastener and the deformation element portion are integrally formed;

at least one body, wherein the body has a first end and a second end, wherein a rod receiving channel for receiving the rod is disposed adjacent the first end of the body, wherein a fastener head receiving chamber is disposed adjacent the second end of the body, wherein the fastener head receiving chamber is tapered towards the second end of the body, and wherein the rod receiving channel and the fastener head receiving chamber are operatively connected; and a compression element which cooperates with the body to push the rod, when the rod is disposed within the rod receiving channel, into contact with at least part of the deformation element portion of the head of the fastener to deform the deformation element portion while pressing the head of the fastener towards the tapered end of the fastener head receiving chamber to fix an angular relationship of the fastener relative to the rod, wherein the deformed deformation element portion comprises a deformed surface shape complementary to a shape of the rod.

18. The fastener assembly of claim 17, wherein the angular relationship of the fastener relative to the rod is fixed at least in part due to: (a) an interference fit between at least a portion of an outside surface of the head of the fastener and at least a portion of an inside surface of the fastener head receiving chamber; and (b) an interference fit between at least a portion of an outside surface of the rod and the deformation element portion of the head of the fastener.

19. The fastener assembly of claim 17, further comprising a retention ring sized to fit at least partially around the head of the fastener when the head of the fastener is disposed within the fastener head receiving chamber.

20. The fastener assembly of claim 19, wherein the angular relationship of the fastener relative to the rod is fixed at least in part due to: (a) an interference fit between at least a portion of an outside surface of the head of the fastener and at least a portion of an inside surface of the retention ring; (b) an interference fit between at least a portion of an outside surface of the retention ring and at least a portion of an inside surface of the fastener head receiving chamber; and (c) an interference fit between at least a portion of an outside surface of the rod and the deformation element portion of the head of the fastener.

21. The fastener assembly of claim 17, wherein the bone connection element of the fastener is selected from the group consisting of: (a) threads; and (b) a hook.

22. The fastener assembly of claim 21, wherein the fastener is configured to be connected to a pedicle portion of the spine.

23. The fastener assembly of claim 22, wherein the fastener is a cannulated bone screw.

24. The fastener assembly of claim 23, wherein the deformation element portion of the head of the cannulated bone screw substantially surrounds the cannulation in the bone screw.

25. The fastener assembly of claim 17, wherein the deformation element portion of the head of the fastener comprises a material which is selected from the group consisting of: (a) a material which is softer than a material from which the rod is formed; and (b) a material which is of essentially the same hardness as a material from which the rod is formed.

26. The fastener assembly of claim 17, wherein the rod receiving channel and the fastener head receiving chamber are operatively connected to allow a tool to be inserted therethrough to apply torque to the fastener.

27. The fastener assembly of claim 26, wherein the head of the fastener is at least partially spherical.

28. The fastener assembly of claim 26, wherein the head of the fastener includes at least one torque receiving feature for receiving torque from the tool.

29. The fastener assembly of claim 28, wherein the torque receiving feature is selected from the group consisting of: (a) at least one indentation; (b) at least one protrusion; and (c) at least one drive face.

30. The fastener assembly of claim 17, wherein the rod has a substantially circular cross section.

31. The fastener assembly of claim 17, wherein the compression element has threads which cooperate with complementary threads of the body.

32. The fastener assembly of claim 31, wherein the compression element has external threads which cooperate with complementary internal threads of the body.

33. A spinal fixation system, comprising:
at least one rod;
at least one screw having a head at a first end, wherein the head of the screw comprises at least one deformation element portion, wherein the deformation element portion comprises an initial undeformed surface shape;
at least one body, wherein the body has a first end and a second end, wherein a rod receiving channel is disposed adjacent the first end of the body, wherein a screw head receiving chamber is disposed adjacent the second end of the body, wherein the screw head receiving chamber is tapered towards the second end of the body, and wherein the rod receiving channel and the screw head receiving chamber are operatively connected; and
a compression element which cooperates with the body to push the rod, when the rod is disposed within the rod receiving channel, into contact with at least part of the deformation element portion of the head of the screw to deform the deformation element portion while pressing the head of the screw towards the tapered end of the screw head receiving chamber to fix an angular relationship of the screw relative to the rod, wherein the deformed deformation element portion comprises a deformed surface shape complementary to a shape of the rod, wherein
the screw is a cannulated bone screw, and
the deformation element portion of the head of the cannulated bone screw is a substantially circular ring protruding from the head of the bone screw.

34. A fastener assembly, comprising:
a rod;
at least one fastener having a head at a first end and a bone connection element at a second end, wherein the head of the fastener comprises at least one deformation element portion and the bone connection element of the fastener is adapted for connection to a spine of a patient, wherein the deformation element portion comprises an initial undeformed surface shape, and wherein the head of the fastener and the deformation element portion are integrally formed;
at least one body, wherein the body has a first end and a second end, wherein a rod receiving channel for receiving the rod is disposed adjacent the first end of the body, wherein a fastener head receiving chamber is disposed adjacent the second end of the body, wherein the fastener head receiving chamber is tapered towards the second end of the body, and wherein the rod receiving channel and the fastener head receiving chamber are operatively connected; and
a compression element which cooperates with the body to push the rod, when the rod is disposed within the rod receiving channel, into contact with at least part of the deformation element portion of the head of the fastener to deform the deformation element portion while pressing the head of the fastener towards the tapered end of the fastener head receiving chamber to fix an angular relationship of the fastener relative to the rod, wherein the deformed deformation element portion comprises a deformed surface shape complementary to a shape of the rod, wherein
the fastener is a cannulated bone screw, and
the deformation element portion of the head of the cannulated bone screw is a substantially circular ring protruding from the head of the bone screw.

* * * * *